United States Patent [19]

Danby

[11] Patent Number: 5,154,700
[45] Date of Patent: Oct. 13, 1992

[54] ARRANGEMENT FOR MONITORING FLUID FLOW DURING INTRAVENOUS SUPPLY TO A PATIENT

[75] Inventor: Hal C. Danby, Sudbury, United Kingdom

[73] Assignee: Danby Medical Limited, Earls Colne, United Kingdom

[21] Appl. No.: 744,350

[22] Filed: Aug. 13, 1991

[30] Foreign Application Priority Data

Aug. 13, 1990 [GB] United Kingdom ............... 9017691

[51] Int. Cl.$^5$ .................... A61M 1/00; A61M 5/00
[52] U.S. Cl. .................... 604/118; 128/DIG. 13
[58] Field of Search .................... 604/118, 67; 128/DIG. 13

[56] References Cited

U.S. PATENT DOCUMENTS

| | | | |
|---|---|---|---|
| 3,335,753 | 8/1967 | Kiser | 128/DIG. 13 |
| 3,863,504 | 2/1975 | Borsanyi | 128/DIG. 13 |
| 4,277,227 | 7/1981 | Jenkins | 604/118 |
| 4,384,578 | 5/1983 | Winkler | 128/DIG. 13 |
| 4,460,355 | 7/1984 | Layman | 604/118 |
| 4,526,574 | 7/1985 | Pekkarinen | 604/118 |
| 4,557,726 | 12/1985 | Reiniche | 604/67 |
| 4,563,179 | 1/1986 | Sakai | 128/DIG. 13 |
| 4,613,325 | 9/1986 | Abrams | 604/118 |
| 4,643,869 | 3/1987 | Bobo, Jr. | 604/118 |
| 4,758,228 | 7/1988 | Williams | 604/118 |
| 4,769,001 | 9/1988 | Prince | 604/118 |
| 4,820,265 | 4/1989 | DeSatnick et al. | 604/118 |
| 4,874,359 | 10/1989 | White et al. | 604/118 |
| 4,950,244 | 8/1990 | Fellincham et al. | 609/118 |

FOREIGN PATENT DOCUMENTS 2157042 10/1985 United Kingdom .

Primary Examiner—Paul J. Hirsch
Attorney, Agent, or Firm—Oblon, Spivak, McClelland, Maier & Neustadt

[57] ABSTRACT

An arrangement for monitoring the pressure of fluid flowing through pliant tubing forming part of a system for the intravenous supply of fluids to a patient under medical treatment in which the tubing is caused to assume an elongate cross-section and a linear voltage displacement transducer having a spring loaded plunger is arranged to apply pressure in a flattened region of the tubing wall to provide indications of contact area movement and thus variations in fluid pressure. Compensation for movement of the contact area after pressure is applied due other than to variations in pressure is provided by a sampler which regularly samples the output of tranducer and provides inputs to a comparator directly and via a shift register so that one sample is compared with an immediately preceding sample. If the difference exceeds the threshold of a threshold circuit, which is indicative of fluid pressure change, an alarm is sounded.

20 Claims, 3 Drawing Sheets

ARRANGEMENT FOR MONITORING FLUID FLOW DURING INTRAVENOUS SUPPLY TO A PATIENT

BACKGROUND OF THE INVENTION

This invention relates to devices and arrangements for monitoring pressure in a fluid flow system and more particularly to such devices and arrangements for use in the intravenous supply of fluids to a patient under medical treatment.

Particularly in such applications as last-mentioned, the fluid flow system will often be of the kind comprising pliant tubing, such as p.v.c. tubing, through which in operation fluid is passed.

SUMMARY OF THE INVENTION

One object of the present invention is to provide improved devices and arrangements for monitoring pressure in a fluid flow system of the above kind.

According to one aspect of this invention, an arrangement for monitoring the pressure of a fluid flowing through pliant tubing according to the present invention includes means for causing the tubing to assume an elongate cross-section over a length thereof, means for applying pressure to an area in a relatively flattened region of the wall of the tubing within the length and responsive to movement thereof to provide indications of variations in the pressure of the fluid and means for compensating for movement of the area occurring after the pressure is applied thereto and due to other than variations in the pressure of the fluid.

In liquid flow systems used in the intravenous supply of liquids to a patient under medical treatment, it is, as previously mentioned, common practice to use p.v.c. tubing in the system. Such tubing is usually treated as "disposable" being changed frequently. For this purpose, p.v.c. tubing is normally regarded as approaching the ideal, being both hygienic and cheap. However, if pressure is applied to an area of its wall and steadily maintained, the wall in the region of the area will firstly yield markedly as the pressure is first applied and then continue to yield decreasingly until it reaches a substantially stable state. With a monitoring arrangement as described above such continued yielding causes continued movement of the area to which the pressure is applied and thus false indications of a variation in the pressure of the fluid. Such continued movement will be slight but it will be appreciated that even slight movements of the wall area due other than to pressure changes in the fluid flowing in the system will produce errors in monitoring which though they may be correspondingly slight may be unacceptable in applications, such as the aforementioned medical application, in which a high level of sensitivity to changes in pressure is required with fluids which in practice will be flowing relatively slowly.

The objective of monitoring movement of an area within a relatively flattened region of the wall of the tubing created by causing the tubing to assume an elongate cross-section over a length thereof is to increase the tendency for movement of the area to occur with changes of pressure of the fluid by destroying the hoop strength of the tubing in that region.

Preferably compensation is provided by means for comparing an indication derived at a given point in time with an indication derived at a previous point in time, and means responsive to the extent of any difference therebetween for signalling that a change in the pressure of the fluid has occurred.

Preferably the indications are produced by sampling at regular intervals from the time that pressure is first applied to the area and continuing beyond the point in time at which the aforementioned substantially stable state is reached. Normally an indication produced by sampling is compared with an immediately preceding indication produced by sampling.

In a practical example using standard p.v.c. tubing of outside diameter 4mm and inside diameter of 3mm, the rate of sampling is approximately once per second.

Preferably the means for causing the tubing to assume an elongate cross-section over a length thereof is a device including a bed member having a non-resilient substantially flat surface across which the tubing may be positioned, means for flattening the tubing non-occlusively over a length thereof against the surface of the bed member and means for applying pressure to a point in a relatively flattened region of the wall of the tubing within the length thereof and responsive to movement thereof to provide an indication of such movement.

Preferably the last-mentioned means includes a linear voltage displacement transducer having a spring-loaded plunger and producing, in operation, an output voltage signal which is indicative of the extent to which the plunger extends beyond the body of the transducer, the plunger being arranged to be pressed into the relatively flattened region of the wall of the tubing at said point.

Preferably the transducer is housed in a body member which is arranged to be moved towards and away from the bed member whereby the tubing may be engaged or released by the plunger.

Preferably the body member includes a tubular projection extending beyond a cylindrical passage within the body member, the passage opening in a surface of the body member facing the bed member, and the tubular projection serving to flatten the tubing as aforesaid as the body member is moved towards the bed member.

Preferably the body member and the bed member are hinged together and means are provided for securing the one to the other when the body member is closed up to the bed member in operation.

In one arrangement in accordance with the present invention the output of the linear voltage displacement transducer arranged to be sampled by a sampling circuit the output of which is connected via an analog-to-digital converter to the input of a unidirectional shift register and in parallel to one input of a comparison circuit a second input for which is derived from the output of the shift register whereby the digitalized output of the sampling circuit is compared with the immediately preceding output of the sampling circuit outputted from the shift register, the output of the comparison circuit being connected via a threshold circuit to operate a suitable alarm.

In other arrangements in accordance with the present invention, constituents of the arrangement as described above connected to take output from the linear voltage displacement transducer and operate the alarm are embodied as a suitably programmed microprocessor.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
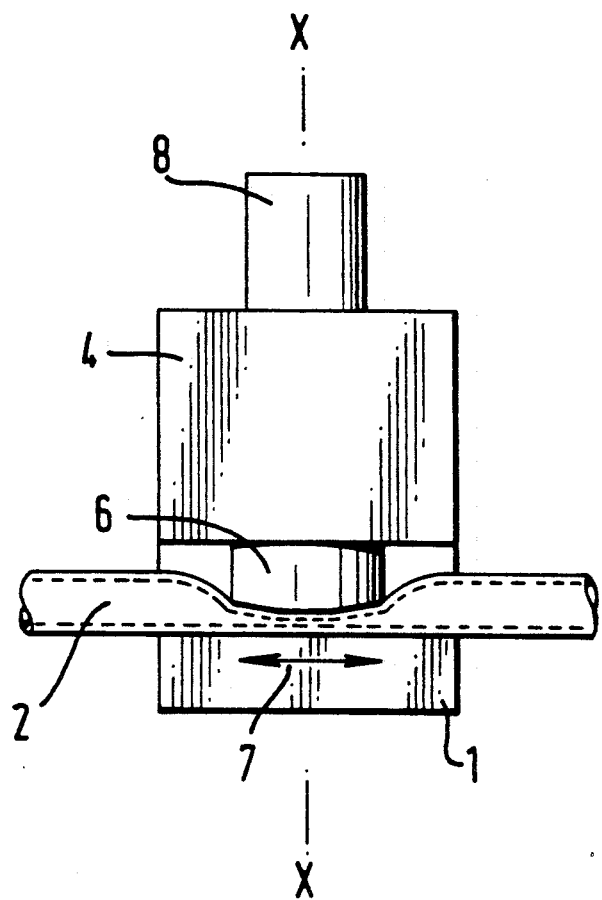
FIG. 1 is a view in elevation of one liquid flow monitoring device in accordance with the present invention.
Figure 2:
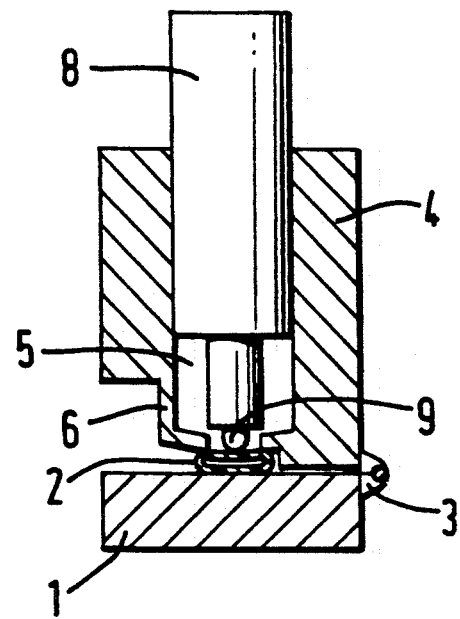
FIG. 2 is a cross-sectional view along the line x—x in FIG. 1.

Referring now to the drawings, wherein like reference numerals designate identical or corresponding parts throughout the several views, and more particularly to FIGS. 1 and 2 thereof, the liquid flow measuring device illustrated thereby includes a hard bed member 1 across the surface of which may be positioned a length of pliant tubing 2, in this case standard pvc tubing of outside diameter 4mm and inside diameter 3mm as used in the intravenous supply of liquid to a patient.

Hinged to the bed member 1 by hinge 3 is a main body member 4 which has a circular cylindrical passage 5 extending orthogonally away from the surface of the bed member 1 across which the tubing 2 is positioned. The passage 5 exits from main body member 4 towards tubing 2 through a tubular projection 6 which, when the main body member 4 is closed up towards the bed member 1, flattens the tubing 2 against the surface of the bed member 1 over a short length 7 thereof. The extent to which tubular projection 6 projects towards bed member 1 is such that when the main body member 4 is fully closed up to the bed member 1 (and held by means of a suitable catch, not represented) the tubing 2 is flattened against the bed member 1 without occlusion occurring and without unduly impeding the flow of liquid through the tubing 2.

Inserted within the passage 5 is a linear voltage displacement transducer 8 of known form. As know per se transducer 8 has a spring-loaded plunger 9 and produces an output digital voltage signal which is indicative of the extent to which plunger 9 extends beyond the body of the transducer 8. The output voltage signal of transducer 8 will thus vary with the displacement of a surface against which plunger 9 is pressed in the direction of action of the plunger 9.

Transducer 8 is entered into and fixed within the passage 5 to an extent such that plunger 9 is spring-biased against the flattened surface of the tubing 2 when the main body member 4 is closed up and secured to the bed member 1, as previously described.

In operation, any variation in the pressure of fluid passing through the tubing 2 will tend to cause expansions and contractions. It is believed that flattening the tubing as above described magnifies the resultant displacement of the relatively flat portion of the wall of the tubing with which the plunger 9 is in contact, thus enabling the transducer 8 to respond to such variations with a higher degree of sensitivity than would otherwise be the case.

Figure 4:
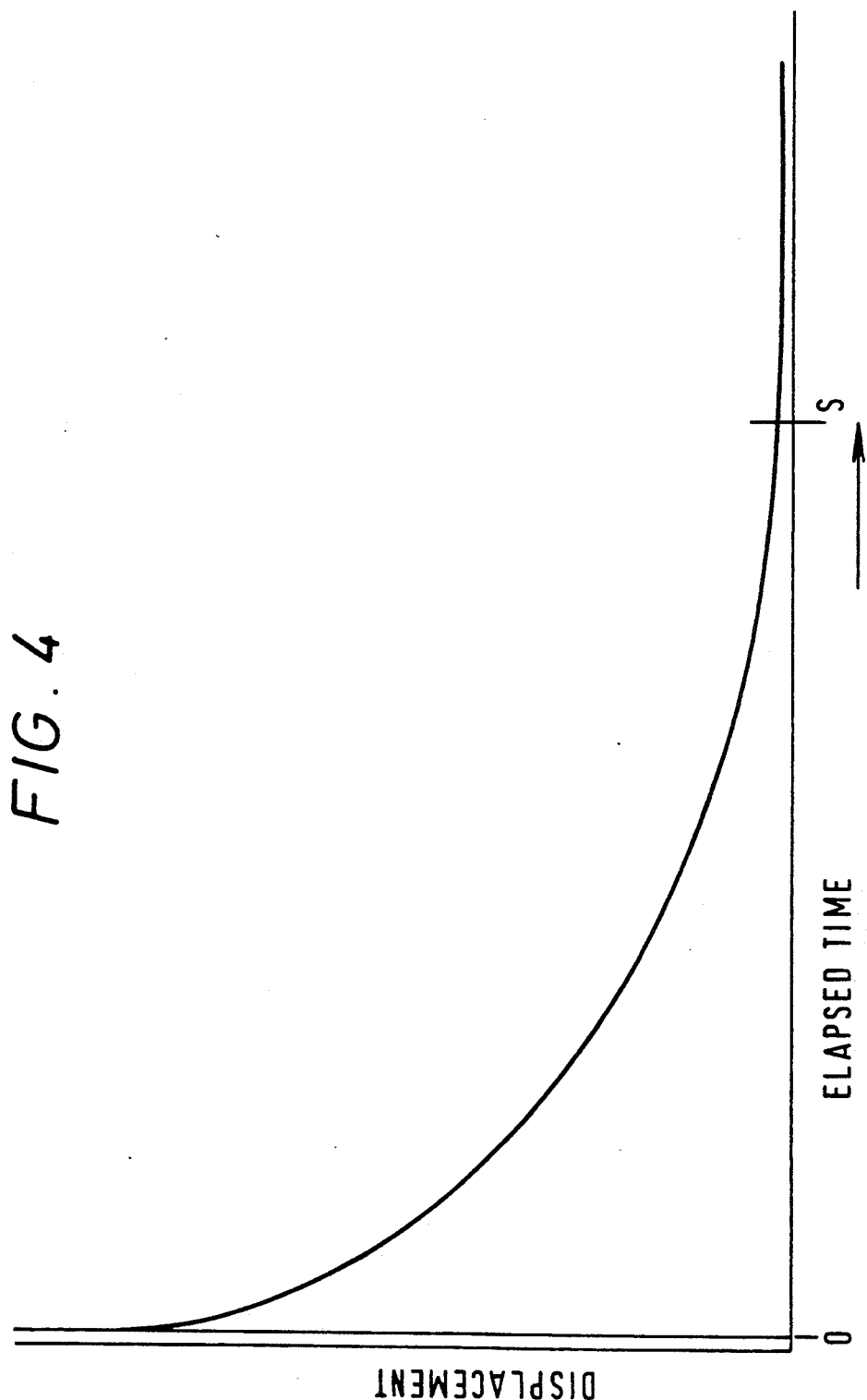
FIG. 4 is a graph illustrating the operation of the device of FIGS. 1 and 2 and the arrangement of FIG. 3.

It has been found that following closing up of the main body member 4 to the bed member 1 a variation in wall displacement will occur, even though the flow of liquid through the tubing 2 remains constant, over a settling down period, as illustrated in the graph of FIG. 4 which represents displacement against time in a typical case. The curve is, it will be noted, of increasingly decreasing slope as time progresses until a point in time at which a relatively stable condition is reached. Typically this is after a period of thirty minutes with an arrangement as described above.

For medical applications such as the intravenous supply of fluid to a patient, as previously mentioned it is required to monitor the flow of fluid through the tubing with a relatively high degree of sensitivity from the moment that the supply is set up. In order to meet this requirement the monitoring device of FIGS. 1 and 2 may be connected in the arrangement illustrated in FIG. 3.

Figure 3:
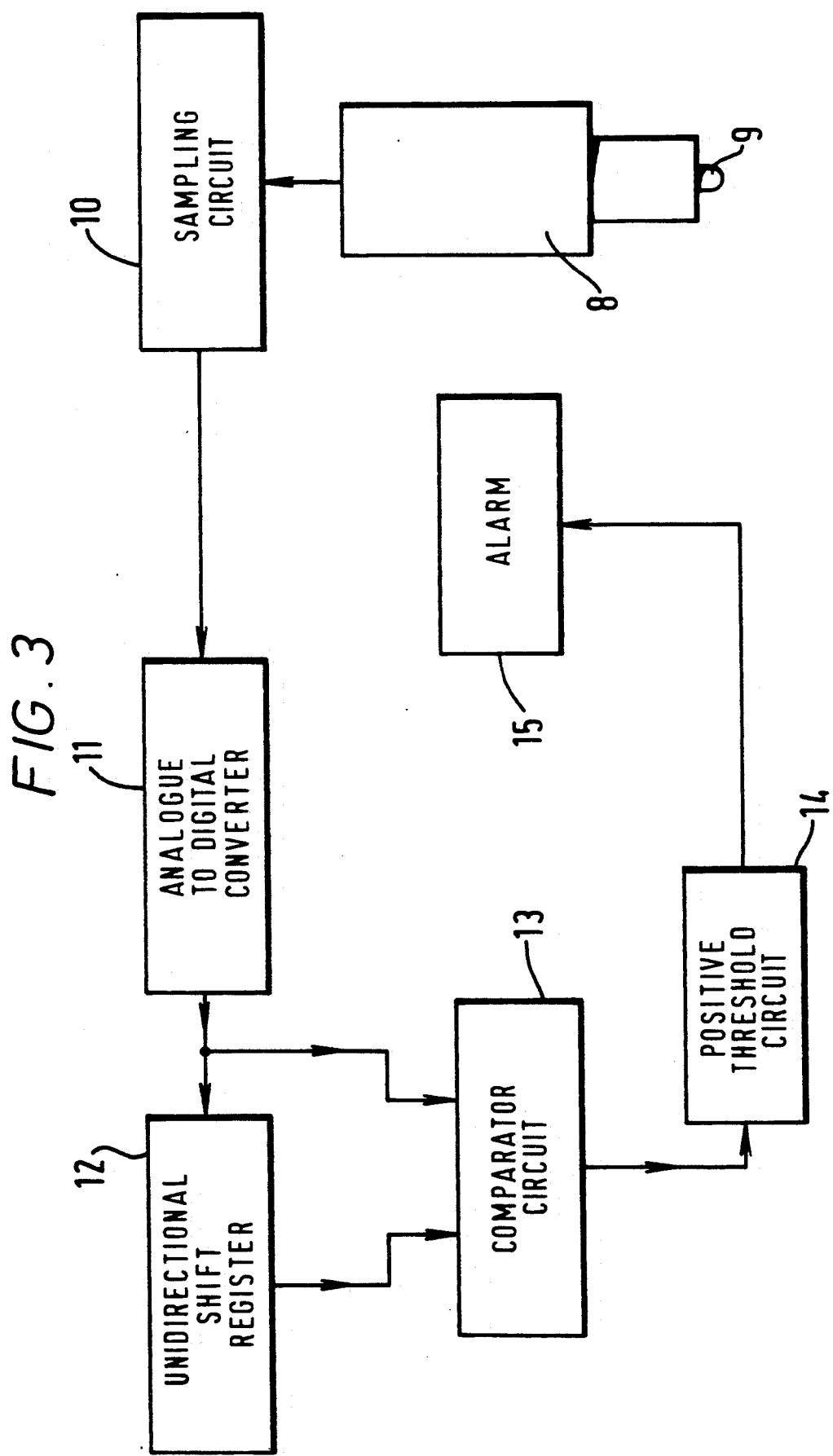
FIG. 3 illustrates in schematic form a liquid flow monitoring arrangement in accordance with the present invention.

Referring to FIG. 3 only transducer 8 and plunger 9 of the monitoring device of FIGS. 1 and 2 are represented. The analog output voltage of transducer 8 is arranged to be sampled at the rate of once per second by a sampling circuit The output of sampling circuit 10 is connected to the input of an analog-to-digital converter 11.

The output of analog-to-digital converter 11 is connected to a unidirectional "count down" only shift register 12, where it is stored, and in parallel to one input of a comparator circuit 13. A second input for comparator circuit 13 is derived from the output of shift register 12 so that comparator circuit 13 compares the digital signal output of analogue-to-digital converter 1 derived from one sample taken by sampling circuit 10 with that derived from the sample taken one second before.

The output of comparator circuit 13 is connected via a positive threshold circuit to a suitable visual and/or aural alarm 15.

An understanding of the operation of the arrangement illustrated in FIG. 3 is assisted by consideration of FIG. 4 which shows a graph of the displacement of the point in the flattened portion 7 of the wall of the tubing 2 into which plunger 9 of transducer 8 is pressed, against time.

As plunger 9 is pressed into the flattened portion 7 of the wall of the tubing 2 (with the flattening itself by tubular projection 6) the wall will first yield markedly over a very short period of time and then, with main body 4 of the monitoring device shown in FIGS. 1 and 2 fully closed up to bed member 1, will continue to yield further, but decreasingly so until a substantially stable state is reached at "S". From zero time to time "S" will typically be thirty minutes. Thus, save as the main body 4 is first closed up to bed member 1, the movement of plunger 9, second by second, will not be great unless there is a change of pressure in the fluid itself. Thus a comparison of the digital signal output of analog-to-digital converter 11 at one sampling with that at the immediately preceding sample one second earlier will show a difference which is above a chosen threshold level (to which threshold circuit 14 is set) only if the pressure in the fluid flowing in the tubing 2 has changed.

Any output from threshold circuit 14 above the set threshold circuit 14 above the set threshold will operate the alarm 15 and may be arranged to trigger any other event as may be desired.

It will be appreciated that the sensitivity of the monitoring arrangement is dependent to a great extent on the number of samples taken by sampling circuit 10. Sensitivity may be increased by increasing the rate of sampling but in practice, with standard p.v.c. tubing as described, once per second has been found to give satisfactory results.

The arrangement of FIG. 3 is a discrete component embodiment.

In other embodiments of the invention (not illustrated) the functions of components 10 to 14 are provided by a suitably programmed microprocessor.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An arrangement for monitoring the pressure of a fluid flowing through a pliant tubing, comprising:
   first means for applying force to at least two spaced apart portions of said tubing for causing said tubing to assume an elongate cross-section over a length of said tubing between said at least two spaced apart portions; and
   second means for applying a pressure unrelated to the force applied by said first means to an area between said at least two spaced apart portions of said tubing within said length and responsive to movement of said area to provide indications of variations in the pressure of said fluid.

2. An arrangement as claimed in claim 1, further comprising:
   means for compensating for movement of said area occurring after said pressure is applied thereto and due to other than variations in the pressure of said fluid.

3. An arrangement as claimed in claims 1 or 2 wherein said pliant tubing is p.v.c. tubing.

4. An arrangement as claimed in claims 1 or 2 wherein said pliant tubing is part of a fluid flow system for the intravenous supply of fluids to a patient under medical treatment.

5. An arrangement as claimed in claims 1 or 2, wherein said compensating means comprises:
   means for comparing an indication derived at a given point in time with an indication derived at a previous point in time; and
   means responsive to the extent of any difference therebetween for signalling that a change in the pressure of said fluid has occurred.

6. An arrangement as claimed in claim 5, wherein the indications are produced by means for sampling at regular intervals from the time that pressure is first applied to said area and continuing beyond the point in time at which the aforementioned stable state is reached.

7. An arrangement as claimed in claim 6, comprising:
   means for comparing an indication produced by sampling with an immediately preceding indication produced by sampling.

8. An arrangement as claimed in claim 6, wherein the rate of sampling is approximately once per second.

9. An arrangement as claimed in claims 1 or 2, wherein said first means comprises:
   a bed member having a non-resilient substantially flat surface across which said tubing may be positioned; and
   means for flattening said tubing non-occlusively over a length thereof against said surface of said bed member;

10. An arrangement as claimed in claim 9, wherein said means for applying pressure comprises:
   a linear voltage displacement transducer having a spring-loaded plunger and producing, in operation, an output voltage signal which is indicative of the extent to which said plunger extends beyond the body of said transducer, said plunger being arranged to be pressed into the relatively flattened region of the wall of said tubing at said point.

11. An arrangement as claimed in claim 10, wherein said transducer is housed in a body member which is arranged to be moved towards and away from said bed member whereby said tubing may be engaged or released by said plunger.

12. An arrangement as claimed in claim 11, wherein said body member comprises:
   a tubular projection extending beyond a cylindrical passage within said body member, said passage opening in a surface of said body member facing said bed member and said tubular projection serving to flatten said tubing as aforesaid as said body member is moved towards said bed member.

13. An arrangement as claimed in claim 10, wherein said body member and said bed member are hinged together and means are provided for securing the one to the other when the body member is closed up to said bed member in operation.

14. An arrangement as claimed in claim 10, wherein the output of said linear voltage displacement transducer is arranged to be sampled by a sampling circuit the output of which is connected via an analog-to-digital converter to the input of a unidirectional shift register and in parallel to one input of a comparison circuit a second input for which is derived from the output of said shift register whereby the digitalized output of said sampling circuit is compared with the immediately preceding output of said sampling circuit outputted from said shift register, the output of said comparison circuit being connected via a threshold circuit to operate a suitable alarm.

15. An arrangement as claimed in claim 14, wherein the constituents connected to take output from said linear voltage displacement transducer and operate said alarm are embodied as a suitably programmed microprocessor.

16. A device for monitoring the pressure of a fluid flowing through a plaint tubing, comprising:
   first means for applying force to at least two spaced apart portions of said tubing for causing said tubing to assume an elongate cross-section over a length of said tubing between said at least two spaced apart portions; and
   second means for applying a pressure unrelated to the force applied by said first means to an area between said at least two spaced apart portions of said tubing within said length and responsive to movement of said area to provide indications of variations in the pressure of said fluid.

17. A device as claimed in claim 16, wherein said second means for applying pressure comprises:
   a linear voltage displacement transducer having a spring-loaded plunger and producing, in operation, an output voltage signal which is indicative of the extent to which said plunger extends beyond the body of said transducer, said plunger being arranged to be pressed into the relatively flattened region of the wall of said tubing at said point.

18. A device as claimed in claim 17, wherein said transducer is housed in a body member which is arranged to be moved towards and away from said bed member whereby said tubing may be engaged or released by said plunger.

19. A device as claimed in claim 18, wherein said body member comprises:

a tubular projection extending beyond a cylindrical passage within said body member, said passage opening in a surface of said body member facing said bed member, and said tubular projection serving to flatten said tubing as aforesaid as said body member is moved towards said bed member.

20. A device as claimed in claim 18, wherein said body member and said bed member are hinged together and means are provided for securing the one to the other when the body member is closed up to said bed member in operation.

* * * * *